United States Patent
Nagata et al.

(10) Patent No.: US 6,267,242 B1
(45) Date of Patent: Jul. 31, 2001

(54) CHEMICAL INDICATOR SHEETS AND PACKAGING BAGS FOR STERILIZATION MADE WITH THE USE OF THE SAME

(75) Inventors: Masanori Nagata; Teiko Sutoh, both of Tokyo; Makoto Sagara, Iwase-mura, all of (JP)

(73) Assignee: Johnson & Johnson Medical Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/403,358

(22) PCT Filed: Apr. 16, 1998

(86) PCT No.: PCT/JP98/01735

§ 371 Date: Oct. 18, 1999

§ 102(e) Date: Oct. 18, 1999

(87) PCT Pub. No.: WO98/46279

PCT Pub. Date: Oct. 22, 1998

(30) Foreign Application Priority Data

Apr. 17, 1997 (JP) .................................................. 9-115167

(51) Int. Cl.⁷ .................................................. B65D 85/00
(52) U.S. Cl. ........................ 206/459.1; 428/35.2; 422/28; 422/56; 436/135
(58) Field of Search ................ 206/459.1, 438; 422/28, 61, 119, 56, 57, 58; 436/135; 428/35.2

(56) References Cited

U.S. PATENT DOCUMENTS

| | | |
|---|---|---|
| 4,478,942 * | 10/1984 | Katsuyama et al. .................... 422/56 |
| 4,481,296 | 11/1984 | Halley . |
| 4,643,876 | 2/1987 | Jacobs et al. . |
| 4,671,936 | 6/1987 | Barron . |
| 4,817,800 | 4/1989 | Williams et al. . |
| 4,855,228 | 8/1989 | Charlton et al. . |
| 5,139,957 | 8/1992 | Grack . |
| 5,620,656 | 4/1997 | Wensky et al. . |
| 5,641,496 * | 6/1997 | Van Roekel .......................... 424/404 |
| 5,942,438 * | 8/1999 | Antonoplos et al. ................... 422/57 |
| 5,955,025 * | 9/1999 | Barrett .................................. 422/28 |

FOREIGN PATENT DOCUMENTS

| | | |
|---|---|---|
| 61-294365 | 12/1961 | (JP) . |
| 64-85127 | 3/1964 | (JP) . |
| 51-40228A | 4/1976 | (JP) . |
| 56-132956 | 10/1981 | (JP) . |
| 59-36172 | 2/1984 | (JP) . |
| 61-287972 | 12/1986 | (JP) . |
| 43827 | 2/1993 | (JP) . |
| 5-65441 | 3/1993 | (JP) . |

\* cited by examiner

*Primary Examiner*—Shian Luong
(74) *Attorney, Agent, or Firm*—Knobbe, Martens, Olson & Bear LLP

(57) ABSTRACT

This invention provides a sheet which has a chemical indicator, in particular, a composition layer for use as an indicator in hydrogen peroxide plasma sterilization, and further provides a packaging bag for said sterilization with use of such an indicator. Said composition layer comprises both a dye which can change color when contacted with hydrogen peroxide vapor or plasma derived from hydrogen peroxide, and a certain organic amine compound.

8 Claims, No Drawings

CHEMICAL INDICATOR SHEETS AND PACKAGING BAGS FOR STERILIZATION MADE WITH THE USE OF THE SAME

This is U.S. national phase under 35 U.S.C. §371 of International Application PCT/JP98/01735, filed Apr. 16, 1998.

TECHNICAL FIELD

This invention relates to a chemical indicator, in particular, a sheet having a composition layer which is useful in a hydrogen peroxide plasma sterilization treatment, and to a packaging bag for such a plasma sterilization treatment which has said composition layer.

BACKGROUND ART

Since long ago, various kind of sterilization means have been applied to articles of every species such as disposable or recyclable medical apparatuses and food containers, and there have also been proposed indicators for conveniently distinguishing whether such a sterilization treatment has been made or not. For example, Japanese Patent Application Laid-Open (Kokai) No. 36172/1984 discloses an indicator for gas sterilization treatment with use of ethylene oxide; and Japanese Patent Application Laid-Open (Kokai) Nos. 287972/1986, 43827/1993 and 65441/1993 each disclose an indicator ink for electron beam sterilization. The latter group of Laid-Open (Kokai) Applications each mention an indicator wherein a pH indicator is used in combination with such a high molecular compound as is capable of generating hydrogen chloride when irradiated with electron beam.

On the other hand, as a means to conduct a sterilization treatment without adversely affecting medical equipments which are produced from various materials, there have recently been proposed and put into practice a hydrogen peroxide plasma sterilization method and an apparatus therefor (See: Japanese Patent Publication (Kokoku) Nos. 62261/1990 and 22693/1995). This sterilization method summarily comprises a step of contacting an article to be sterilized, with hydrogen peroxide vapor under reduced pressure in an air-tight chamber, and then generating hydrogen peroxide plasma. This method can be said to be a very useful one, not only in that high sterilization efficiency is attained but also in that, when plasma state is ended, hydrogen peroxide is converted into water and oxygen which are quite harmless.

The above-mentioned Japanese Patent Publication (Kokoku) No. 22693/1995 discloses a liquid-dispensing cassette to be used in a plasma sterilization apparatus which cassette is equipped with a cell for containing a hydrogen peroxide solution. It is further disclosed that said dispensing cassette may be equipped with an indicator strip having a color tone with which to detect the leakage of hydrogen peroxide solution from the liquid-containing cell. Said Publication does not concretely disclose, however, how to constitute the indicator strip.

Also in putting a hydrogen peroxide plasma sterilization method into practice, it would be desirable that there should be available such an indicator which can easily distinguish whether or not a sterilization treatment has been given to an article to be sterilized, as is employed in the aforementioned gas sterilization treatment with use of ethylene oxide or electron beam sterilization treatment. Thus, the object of this invention is to provide both a sheet having a chemical indicator composition layer (or an indicator function layer) which can distinguish whether or not a hydrogen peroxide plasma sterilization treatment has been given to an article to be sterilized, and a packaging bag for plasma sterilization having said composition layer.

DISCLOSURE OF INVENTION

The aforementioned Japanese Patent Application Laid-Open (Kokai) No. 65441/1993, for example, suggests that, when bisphenols and a substance such as triphenylsulfonium hexafluorophosphate which generates acid or free radical when irradiated with electron beam are compounded with an indicator ink which comprises a pH indicator and such a high molecular compound as generates hydrogen chloride when irradiated with electron beam, there can be improved the color changeability of said ink when irradiated with electron beam. The inventors of the present invention, on the other hand, have found out that, when a dye belonging to a specific pH indicator is brought into contact with a system which comprises hydrogen peroxide and plasma derived from hydrogen peroxide and which does not generate hydrogen chloride, there occurs a certain color change, which can be both stabilized and rendered distinct when a certain organic amine is made to co-exist.

Thus, in order to achieve the above-mentioned object, this invention provides a sheet used for distinguishing whether a hydrogen peroxide plasma sterilization treatment has been made or not, which sheet has, on its substrate, an indicator composition layer and, under circumstances, an overcoat layer which is provided on said indicator composition layer, the indicator composition layer containing a dye which can change its color when contacted with at least one substance selected from the group consisting of hydrogen peroxide and plasma derived from hydrogen peroxide, an organic amine compound which does not evaporate under ambient conditions, aliphatic alcohol(s) and a synthetic resin which is soluble in said alcohol(s).

This invention which has the aforementioned features makes it possible to clearly distinguish whether medical apparatuses, food containers and the like have undergone or not such a hydrogen peroxide plasma sterilization treatment, even after a certain time has passed from said treatment.

DETAILED DESCRIPTION OF INVENTION

As for the dye, in the indicator composition layer of this invention, which can change its color when contacted with at least one substance selected from the group consisting of hydrogen peroxide and plasma derived from hydrogen peroxide, there can be employed dyes of any kind so long as they make it possible, owing to tr change in color before and after said contact, to clearly distinguish whether such a contact has been made or not. As typical examples of such dyes, there can be taken, not restrictively, pH indicators which have a transition interval in a range of pH 5.5 to 9.0. Concrete examples of such pH indicators include 1,2-dihydroxy anthraquinone (pH 5.5–6.8); dibromothymol sulfonphthalein (Bromothymol Blue: pH 6.0–7.5); 5,8-quinolinequinon-8-hydroxy-5-quinolyl-5-imide (pH 6.0–8.0); 3-amino-6-dimethylamino-2-methylphenazine hydrochloride (pH 6.8–8.0); phenolsulfonphthalein (Phenol Red pH 6.8–8.4); o-cresolsulfon phthalein (Cresol Red: pH 7.2–8.8); m-cresolsulfon phthalein (pH 7.4–9.0) and the like, and tr derivatives. In practical use, two or more of these indicators may be combined with one another.

This invention is characterized in that the above dye is used along with an organic amine compound which does not evaporate under ambient conditions (concretely, at a room temperature at which the sterilization treatment is made). Any kind of such organic amine compounds are usable so long as they do not evaporate throughout sterilization treatment, in particular a low temperature sterilization treatment with use of hydrogen peroxide (See: for example, Japanese Patent Publication (Kokoku) No. 62261/1990; Thus cited, this Publication constitutes a part of the present invention), and so long as they can adjust pH of the composition to alkaline side. Examples of such organic amine compounds include mono higher aliphatic amine such as laurylamine, mono hydroxy higher aliphatic amine, triethanol amine, diethanol amine and monoethanol amine. Among these, triethanol amine is preferably employed in particular, in consideration of compatibility with the dye used in this invention and compatibility with synthetic resin which may be included as vehicle in the composition.

The indicator composition layer of this invention can usually contain a vehicle (including synthetic resin, solvent, and, if necessary, plasticizer as well), which is normally used for the preparation of printing ink, and additive (such as dispersant, stabilizer and thickening agent), and, further, in particular, aliphatic alcohol(s) and a synthetic resin which is soluble in said alcohol(s), for example, polyamide resin.

As for typical example of such synthetic resin, polyamide resin which is normally used for the preparation of printing ink is conveniently employed. As for solvent, isopropyl alcohol, n-propyl alcohol, n-butyl alcohol, etc. can be used. Concrete examples of polyamide resin include such a polyamide resin as is produced by polycondensation of aliphatic dicarboxylic acid and aliphatic diamines each of which has an average molecular weight of 10,000 to 50,000. Typical examples of such resin on the market include polyamide resins which are being sold by Sanwa Chemical K.K. under trade names such as SUNMIDE 611DK-1, by Sanyo Kasei K.K. under trade names such as POLYMIDE S-40E and by Toyama Kasei K.K. under trade names such as TOMIDE 395, respectively. These resins may be used either singly or in combination of two or more thereof The above-mentioned composition may comprise 0.3–10% by weight of dye, 3–30% by weight of organic amine compound, 10–60% by weight of aliphatic alcohol, 15–45% by weight of polyamide resin, and, under circumstances, 0.3–10% weight of ultraviolet light absorber as well, each on the basis of the total weight of the composition.

In this invention, chemical indicator composition layer may be formed on a substrate to give an indicator-function layer, and, under circumstances, an overcoat layer may be provided on said indicator-function layer. The overcoat layer may be formed from any components so long as the resulting layer is permeable to hydrogen peroxide vapor or plasma derived from hydrogen peroxide, and so long as said formed layer is transparent or semi-transparent such that the color change of dye can be seen through. In view of adhesion with indicator function layer, however, the overcoat layer is preferably formed from a composition which contains those components to form the indicator-function layer, except dye but including ultraviolet light absorber instead, and, under circumstances, further including 0.3–10% by weight of wax (e.g., polyethylene wax) on the basis of the total amount of the composition. The formation of overcoat layer can in particular prevent physical injury of indicator-function layer.

As for ultraviolet light absorber, those of any species may be employed so long as they are normally used in this field and unless they have adverse effects in view of achievement of the object of this invention. For example, benzotriazole derivatives on the market are preferably used. Typical examples of said derivatives include Tinuvin type compounds having sunscreen property produced by Ciba-Geigy, which are to be employed singly or in combination of two or more of them.

The sheet comprising thus formed two layers may either take a strip-like form or constitute a part of a packaging bag for packing articles to be sterilized.

As another embodiment therefore, the present invention provides a packaging bag with an indicator for sterilizing its contents with hydrogen peroxide plasma, wherein there is deposited, on at least a part of said packaging bag, a composition layer for use as a chemical indicator which comprises both a dye which can change its color when contacted with at least one substance selected from the group consisting of hydrogen peroxide and plasma derived from hydrogen peroxide, and an organic amine compound which does not evaporate under ambient conditions, and wherein at least a part of said packaging bag is made of breathing sheet.

The packaging bag of the present invention is at least partly constituted of breathing material. As for breathing sheet, there is preferably employed a material which is impermeable to microorganisms, has heat sealability and breathability (preferably of at most 100 seconds; JIS-P-8117), and is resistant to hydrogen peroxide and plasma derived from hydrogen peroxide both of which are main components of sterilizing gas. Examples of such a material include non-woven fabric made from high density polyethylene, polypropylene, and the like. It is preferable in particular to use TYVEK, a non-woven fabric of high density polyethylene which is sold by DuPont Japan Limited.

The other portions of the above packaging bag may be constituted of a composite laminate sheet which is prepared by laminating heat-sealable films such as low density polyethylene, polypropylene, and the like, on a polyester film or the like as a base material. The use of such films makes it possible to see contents through the bag.

Such a packaging bag is made in the following manner: (i) as a usual process, both a breathing sheet such as non-woven fabric and a plastic film laminate sheet are heat-sealed at necessary end portions; (ii) a laminate sheet is folded down, and two ends are made to face each other, and, then, a breathing sheet is placed over the gap between said two ends, and, then, necessary portions are heat-sealed; or (iii) a breathing sheet is employed for bottom of a self-supporting bag.

The indicator-function layer is normally formed on the surface of a breathing sheet. When packaging bag is so transparent as to show its interior, indicator-function layer may be formed either on the inner side of breathing sheet, or on the inner side of laminate sheet, i.e., inside the packaging bag. In this case, however, attention should be paid so that contents may not be contaminated.

The above-mentioned composition layer of this invention is homogenized by such a known kneading method as is employed for the preparation of printing ink, and is then deposited on a substrate by an also known printing method, e.g., offset printing, flexographic printing or gravure printing, to form an indicator-function layer, and, subsequently, under circumstances, an overcoat layer is formed, and, thus, the sheet of this invention can be produced. The amount of indicator-function layer adhered is, although not restricted, generally 2–20 $g/m^2$, preferably 3–15 $g/m^2$. When the amount adhered is less than 2 $g/m^2$, color change after treatment is apt to be difficult to be confirmed, while, when it exceeds 20 $g/m^2$, scratches are liable to be formed during transportation or storage.

EXAMPLES

In the following, this invention is explained in more detail with concrete examples. Percentage in the examples mean "% by weight" unless otherwise specified.

Example 1
Formation of Indicator-function Layer and Overcoat Layer
A composition having the following components:

| | |
|---|---|
| POLYMIDE S-40E | 20.0 (%) |
| (a polyamide resin made by Sanyo Kasei K. K.) | |
| Isopropyl alcohol | 47.0 |
| n-Propyl alcohol | 20.0 |
| Triethanol amine | 10.0 |
| Phenol Red (including no acid) | 2.0 |
| Tinuvin 328 | 1.0 |
| (an ultraviolet light absorber produced by Ciba-Geigy) | |
| Total | 100.0 | was mixed and kneaded by an enclosed ball mill until the composition became homogeneous, and, thus, a composition for indicator was prepared.

Apart from the above, a composition having the following components:

| | |
|---|---|
| POLYMIDE S-40E | 20.0 (%) |
| Isopropyl alcohol | 46.5 |
| n-Propyl alcohol | 20.0 |
| Triethanol amine | 10.0 |
| Tinuvin 328 | 1.0 |
| Polyethylene wax | 2.5 |
| Total | 100.0 | was treated in the same manner as in the above composition for indicator, and, thus, a composition for overcoat was prepared.

Example 2
Preparation and Evaluation of Chemical Indicator

The composition for indicator and the composition for overcoat both of which had been prepared in accordance with Example 1 were placed on the surface of a non-woven fabric of high density polyethylene by gravure method with use of a gravure roll. The amount of the composition for indicator adhered (solid) and the amount of composition for overcoat adhered (solid) are shown together in Table 1.

As for evaluation, the above-mentioned non-woven fabric was put in STERRAD-100 (LOW Temperature Plasma Sterilization System by Johnson & Johnson Medical Co.), and was subjected to sterilization treatment for 75 minutes, and, thus, the degree of color change of the indicator layer by was visually observed. Moreover, said non-woven fabric was irradiated with ultraviolet light for 30 minutes with use of Sunshine-type Weather-Ometer produced by Suga Tester K.K., and, thus, the degree of color change of the indicator layer was visually observed. The results are shown together in Table 1.

Evaluation was made according to the following standard:

(Color Changeability)
  ○--- Changed to slightly red-tinted yellow or to light yellow
  ⊙--- Changed to yellow (Weatherability)
  ○--- Although slightly faded, practically no problem.
  ⊙--- Not added at all.

TABLE 1

| Sample No. | Amount of indicator adhered (g/m$^2$) | Amount of overcoat adhered (g/m$^2$) | Color changeability | Weatherability |
|---|---|---|---|---|
| (This invention) | | | | |
| 1 | 4 | 1 | ⊙ | ○ |
| 2 | 6 | 1 | ⊙ | ○ |
| 3 | 8 | 2 | ⊙ | ⊙ |
| 4 | 10 | 2 | ⊙ | ⊙ |
| (Comparison) | | | | |
| 1 | 1 | 1 | X | ○*1) |
| 2 | 25 | 1 | ⊙ | ○*2) |

*1) Color change was hard to confirm.
*2) Printed surface was injured, and indicator dropped off.

Example 3
Effects of Sterilization Treatment, and Color Change of Indicator

There was applied, by gravure method, 15 g (wet)/m$^2$ of the indicator ink of this invention on one surface of a non-woven fabric of high density polyethylene. Then, said non-woven fabric with an indicator was superposed on a laminate sheet composed of a polyester film as outside film and a low density polyethylene film as inside film, and three sides were heat-sealed to give a sterilizing bag. Into this sterilizing bag, there were put a 50 ml plastic syringe and a biological indicator (BI), which were then sterilized by means of STERRAD-100 (LOW Temperature Plasma Sterilization System by Johnson & Johnson Medical Co.) for 75 minutes. Said BI, for which a test pack of sporangium (Standard Microorganism No. ATCC 9372) had been employed, was taken out in a germ-free manner after sterilized by the above-mentioned Low Temperature Plasma Sterilization System, and was then planted on a sterilized TSB medium. After culturing at 35° C. for seven days, it was visually confirmed whether any microorganism had grown. It was found resultantly that the color of the indicator applied on the non-woven fabric had changed from reddish violet (before sterilization) to yellow (after sterilization), and also that BI showed no growth of microorganism. It was confirmed from the above facts that it can be distinguished, at the time when the sterilizing bag of this invention is opened, whether packed articles such as medical instruments have undergone a sterilization treatment or not.

Industrial Applicability

This invention provides a sheet which has thereon a composition layer which makes it possible to clearly distinguish whether packed articles such as medical instruments have undergone a sterilization treatment or not, and further provides a packaging bag for medical instruments which bag has, in at least a part thereof, such a composition layer as mentioned above. Hence, this invention is applicable both in the field of medical treatment and in the field of the production of medical instruments.

What is claimed is:
1. A sheet used for monitoring the efficacy of a hydrogen peroxide plasma sterilization treatment, said sheet comprising an indicator-function layer, said indicator-function layer comprising:
   a dye which can change color when contacted with at least one substance selected from the group consisting of hydrogen peroxide and plasma derived from hydrogen peroxide, an organic amine compound which does not evaporate under ambient conditions, at least one aliphatic alcohol, and a synthetic resin which is soluble in said alcohol.

2. The sheet of claim 1, further comprising an overcoat layer which is provided on said indicator-function layer.

3. A sheet used for monitoring the efficacy of a hydrogen peroxide plasma sterilization treatment, said sheet comprising:

an indicator-function layer comprising:
- a dye which can change color when contacted with at least one substance selected from the group consisting of hydrogen peroxide and plasma derived from hydrogen peroxide;
- an organic amine compound which does not evaporate under ambient conditions:
- at least one aliphatic alcohol:

a synthetic resin which is soluble in said alcohol; and an overcoat layer which is provided on said indicator-function layer, said overcoat layer comprising:
- at least one aliphatic alcohol,
- a synthetic resin which is soluble in said alcohol,
- ultraviolet light absorber, and
- waxes.

4. The sheet of claim 1 wherein the aliphatic alcohol(s) is $C_{3-5}$ alcohol(s) and wherein the synthetic resin is polyamide resin.

5. A packaging bag for sterilizing its contents with hydrogen peroxide plasma, wherein there is deposited, on at least a part of said packaging bag, a composition layer for use as a chemical indicator which comprises both a dye which can change its color when contacted with at least one substance selected from the group consisting of hydrogen peroxide and plasma derived from hydrogen peroxide, and an organic amine compound which does not evaporate under ambient conditions, and wherein at least a part of said packaging bag is made of breathing sheet.

6. The packaging bag of claim 5 wherein the composition layer for use as a chemical indicator further contains aliphatic alcohol(s) and a synthetic resin which is soluble in said alcohol(s) as well.

7. The packaging bag of claim 5 wherein the composition layer for use as a chemical indicator is deposited in the form of a thin layer on one side of the breathing sheet.

8. The packaging bag of any one of claims 5 wherein the breathing sheet is made of nonwoven fabric produced from high-density polyethylene or polypropylene.

* * * * *

UNITED STATES PATENT AND TRADEMARK OFFICE
CERTIFICATE OF CORRECTION

PATENT NO.   : 6,267,242 B1
DATED        : July 31, 2001
INVENTOR(S)  : Masanori Nagata, Teiko Sutoh, and Makoto Sagara It is certified that error appears in the above-identified patent and that said Letters Patent is hereby corrected as shown below:

<u>Column 8,</u>
Line 21, delete "any one of claims" and insert therefor -- claim --

Signed and Sealed this

Sixteenth Day of April, 2002

*Attest:*

*Attesting Officer*

JAMES E. ROGAN
*Director of the United States Patent and Trademark Office*